United States Patent [19]

Moore

[11] 4,124,725
[45] Nov. 7, 1978

[54] ANTI-INFLAMMATORY METHOD

[75] Inventor: George G. I. Moore, Birchwood, Minn.

[73] Assignee: Riker Laboratories, Inc., Northridge, Calif.

[21] Appl. No.: 797,173

[22] Filed: May 16, 1977

[51] Int. Cl.² ............................................. A61K 31/135
[52] U.S. Cl. ..................................................... 424/330
[58] Field of Search ......................................... 424/330

[56] References Cited

U.S. PATENT DOCUMENTS

| | | | |
|---|---|---|---|
| 3,711,554 | 1/1973 | Engelhardt et al. | 260/591 |
| 3,932,324 | 1/1976 | Stretanski | 260/23H |

OTHER PUBLICATIONS

J.A.C.S., 95, pp. 4698–4705 (1973).
J. Org. Chem. 33: 1245–1246(1968).
J.A.C.S. 79: 5019–5023 (1957).
Chem. Abst., Formula Index $C_{19}$–$C_{22}$ 8th Col. p. 8408F.

Primary Examiner—Stanley J. Friedman
Attorney, Agent, or Firm—Cruzan Alexander; Donald M. Sell; Donald C. Gipple

[57] ABSTRACT

Compounds in which 2,6-di(t-butyl)phenol is substituted in the 4 position by an optionally substituted benzoyl group have valuable pharmacological activity as anti-inflammatory agents.

1 Claim, No Drawings

ANTI-INFLAMMATORY METHOD

BACKGROUND OF THE INVENTION

This invention relates to the use of 4-benzoyl-2,6-di(t-butyl)phenols as anti-inflammatory agents.

Compounds such as 4-benzoyl-2,6-di(t-butyl)phenol (German Offenlegungschrift No. 1,811,322) and 4-(2-hydroxybenzoyl)-2,6-di(t-butyl)phenol (French Pat. No. 1,326,292) are known to the art (see, for example, J. Am. Chem. Soc. 79:5019, 1957). No physiological use of such compounds has been reported, however.

DETAILED DESCRIPTION OF THE INVENTION

This invention relates to a method for combatting inflammatory processes in mammalian animals by administering thereto an effective dose, less than the toxic amount, of a 2,6-di((t-butyl)phenol which is substituted in the 4 position by an optionally substituted benzoyl group. The invention also relates to anti-inflammatory compositions comprising one or more 2,6-di(t-butyl)-phenols substituted in the 4 position by an optionally substituted benzoyl group together with a suitable pharmaceutical extending medium.

Specifically the invention relates to a method for combatting inflammatory processes in mammalian animals which comprises administering thereto an effective dose, less than the toxic amount, of a compound of the formula:

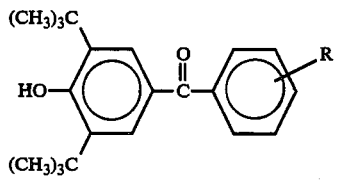

wherein R is hydrogen, 2- or 4-fluoro, alkoxy of 1 to 3 carbon atoms, hydroxy, amino or methylthio. In addition to their anti-inflammatory activity, some of these compounds are also analgesic and antipyretic agents and some have mild immunosuppressant activity.

In order to determine and assess pharmacological activity, testing in animals is carried out using various assays known to those skilled in the art. Thus, the anti-inflammatory activity of the compounds can be conveniently demonstrated using an assay designed to test the ability of these compounds to antagonize the local edema which is characteristic of the inflammatory response (the rat foot edema test). The compounds (I above) have also been found to inhibit the enzyme prostaglandin synthetase. Such topical activity has been measured by means of the guinea pig erythema test and by a contact sensitivity test. Anti-inflammatory activity may also be detected by other assays known to the art such as the cotton pellet granuloma test and the adjuvant arthritis test. The analgesic activity has been observed in standard test methods such as the phenylquinone writhing (mouse) and Randall-Selitto (rat) tests.

Leading references to the rat foot edema method are:
(1) Adamkiewicz et al, Canad. J. Biochem. Physio. 33:332, 1955;
(2) Selye, Brit. Med. J. 2:1129, 1949; and
(3) Winter, Proc. Exper. Biol. Med. 111:544, 1962.

The edema test is performed on adult female rats. One group of 10 rats serves as non-medicated controls, while another group of 10 rats receives the test compound at various times prior to the induction of the edema, usually 15 minutes, one hour and/or 18 hours. The test compound is administered orally as a suspension in 4 percent aqueous solution of acacia. Edema is induced by the plantar injection of 0.5 percent carrageenin (0.1 ml/foot) into the right hind foot. The left hind foot receives a like volume of 0.9 percent saline solution. One hour later, the volume of each hind foot is determined plethysmographically. The edema is expressed as the increase in the volume of the edemogen-injected foot (volume of the "edemogen foot" less the volume of the "saline foot"). The percent inhibition is calculated by dividing the mean increase in the edema of the edemogen foot of the medicated group by the mean increase in the non-medicated group, multiplied by 100. An active dose is that giving a statistically significant inhibition of the induced edema, usually in the range of about 25–35 percent inhibition.

The compounds are preferably administered orally as anti-inflammatory agents but other known methods of administration are contemplated as well, e.g. dermatomucosally (for example dermally, rectally and the like) and parenterally, for example by subcutaneous injection, intramuscular injection, intra-articular injection, intravenous injection and the like. Ocular administration is also included. Dosages ordinarily fall within the range of about 1 to 500 mg/kg of body weight of the mammal to be treated although oral dosages are not usually above 100 mg/kg. Suitable forms for oral administration include liquids (such as 4 percent acacia and polyethylene glycol solutions), tablets (which may contain anhydrous lactose, microcrystalline cellulose, modified starch, calcium stearate and talc, as well as other conventional compounding agents together with the active anti-inflammatory agents), solid suspensions and capsules. Suitable carriers for topical application include creams, gels, tapes and the like. Liquid formulations, such as solutions or suspensions of the active ingredient in inert carriers, are contemplated for dosage by injection.

The compounds which are presently preferred for use in the process of the invention (due to their high oral activity) are:
4-benzoyl-2,6-di(t-butyl)phenol,
4-(4-fluorobenzoyl)-2,6-di(t-butyl)phenol,
4-(4-hydroxybenzoyl)-2,6-di(t-butyl)phenol,
4-(4-aminobenzoyl)-2,6-di(t-butyl)phenol,
4-(2-methoxybenzoyl)-2,6-di(t-butyl)phenol, and
4-(2-hydroxybenzoyl)-2,6-di(t-butyl)phenol.

The compounds used in the method of the invention may be prepared using methods described in the prior art or by chemical reaction of compounds described in the prior art. Alternatively, some of the compounds are further utilized as intermediates to prepare others. Many of the compounds are conveniently prepared by reaction of 2,6-di(t-butyl)phenol with an appropriately substituted benzoyl chloride in the presence of a Friedel-Crafts solvent such as dichloroethylene, carbon disulfide and the like. These reactions are typically carried out at temperatures of 0° to 100° C. Another useful synthetic method is the reaction of n-butyl lithium with 2,6-di(t-butyl)phenol in glyme followed by reaction with a substituted benzoyl chloride at a moderate temperature, for example from about 20° to 200° C.

The following non-limiting examples are illustrative of the preparation of the compounds which are utilized in the method of the invention.

EXAMPLE 1

A solution of 50 g. of 4-methylthiobenzoic acid in dichloromethane is treated with excess thionyl chloride at its reflux temperature until no acid remains (according to infrared spectral analysis). Distillation at reduced pressure (b.p. 140° C./0.2 mm. Hg) provides a clear liquid which gradually solidifies to provide 4-methylthiobenzoyl chloride.

A solution of 54.5 g. (0.29 mole) of 4-methylthiobenzoyl chloride in 200 ml. of dichloroethylene is added gradually to 55 g. (0.29 mole) of titanium tetrachloride. After cooling this mixture, a solution of 60 g. of 2,6-di(t-butyl)phenol in 200 ml. of dichloroethylene is added. The resulting mixture is stirred for several hours, then hydrolyzed with 10 percent hydrochloric acid. The organic layer is separated, washed with water, dried and evaporated to provide a yellow oil. This product is mixed with hexane to provide a white solid which is recrystallized from hexane to provide 4-(4-methylthiobenzoyl)-2,6-di(t-butyl)-phenol, m.p. 135°–136° C.

| Analysis: | | %C | %H |
|---|---|---|---|
| Calculated for $C_{22}H_{28}O_2S$: | | 74.1, | 7.9 |
| | Found: | 73.4, | 8.0. |

Using the method of Example 1, the benzoyl chloride derivatives shown in Table I are reacted with 2,6-di(t-butyl)phenol to provide products of the invention.

TABLE I

| Ex. No. | Substituted Benzoyl Chloride Starting Material | Product |
|---|---|---|
| 2 | 2-fluorobenzoyl chloride | 4-(2-fluorobenzoyl)-2,6-di-(t-butyl)phenol m.p.127–129° C. |
| 3 | 4-fluorobenzoyl chloride | 4-(4-fluorobenzoyl)-2,6-di(t-butyl)phenol m.p. 133.5–135° C. |
| 4 | 2-methoxybenzoyl chloride | 4-(2-methoxybenzoyl)-2,6-di(t-butyl)phenol m.p. 101–102° C. |
| 5 | benzoyl chloride | 4-benzoyl-2,6-di(t-butyl)phenol m.p. 125–127° C. |

EXAMPLE 6

A slurry of 22.5 g. (0.15 mole) of 4-methoxybenzoic acid in benzene at reflux is treated with 12.5 ml. (0.15 mole) of thionyl chloride and 1 ml. of N,N-dimethyl formamide. After stirring for 15 minutes the solution is evaporated and cooled to provide 4-methoxybenzoyl chloride as a yellow solid. The solid is dissolved in carbon disulfide and added to 20 g. (0.15 mole) of aluminum chloride slurried in 200 ml. of carbon disulfide. To this mixture is added 30 g. (0.15 mole) of 2,6-di(t-butyl)-phenol. After stirring for 2 hours at room temperature, the resulting mixture is poured into a dilute hydrochloric acid-ice mixture, then extracted with three portions of dichloromethane. The organic layer is dried, then evaporated to provide a residue which is recrystallized twice from a benzene-hexane mixture to provide 4-(4-methoxybenzoyl)-2,6-di(t-butyl)phenol, m.p. 141°–142.5° C.

| Analysis: | | %C | %H |
|---|---|---|---|
| Calculated for $C_{22}H_{28}O_3$: | | 77.7, | 8.3 |
| | Found: | 77.8, | 8.5. |

EXAMPLE 7

To a stirred solution of 2,6-di(t-butyl)phenol in 150 ml. of glyme under nitrogen is added 52 ml. of 2.04M n-butyl lithium in hexane. The reaction causes an exotherm and the product is heated to 60° C. About 20 g. of 4-nitrobenzoyl chloride is added, and the resulting solution is stirred without heating for about 16 hours. The mixture is then acidified with 10 percent hydrochloric acid and washed with dichloromethane, then with 10 percent sodium hydroxide solution and finally with water. The solution is then reacted in ethanol with 50 percent sodium hydroxide solution by heating at reflux for about two hours, mixed with dichloromethane, then washed several times with water. The organic layer is separated, dried and evaporated to provide an orange oil which solidifies in cold hexane. This solid is recrystallized from a benzene-hexane mixture to provide 4-(4-nitrobenzoyl)-2,6-di(t-butyl)phenol, m.p. 178°–179.5° C.

| Analysis: | | %C | %H | %N |
|---|---|---|---|---|
| Calculated for $C_{21}H_{25}NO_4$: | | 71.0, | 7.1, | 3.9 |
| | Found: | 71.7, | 7.2, | 3.8. |

EXAMPLE 8

To a freshly prepared, stirred solution of 0.25 mole of sodium ethanethiolate in 250 ml. of N,N-dimethylformamide at 0° C. is added 34 g. (0.10 mole) of 4-(4-methoxybenzoyl)-2,6-di(t-butyl)phenol, and the resulting solution is refluxed for 3 hours. The solution is stirred at 23° C. for about 16 hours, then acidified with 10 percent hydrochloric acid and extracted with dichloromethane. The organic extracts are washed twice with 10 percent hydrochloric acid, then with water, then dried and evaporated to provide an oil residue. The residue is dissolved in benzene and cooled. A solid crystallizes after many hours. It is recrystallized from a benzene-hexane mixture, then sublimed to provide white crystals of 4-(4-hydroxybenzoyl)-2,6-di(t-butyl)-phenol, m.p. 188°–189.5° C.

| Analysis: | | %C | %H |
|---|---|---|---|
| Calculated for $C_{21}H_{26}O_3$: | | 77.3, | 8.0 |
| | Found: | 77.0, | 8.1. |

EXAMPLE 9

Similarly, 4-(2-hydroxybenzoyl)-2,6-di(t-butyl)-phenol, m.p. 126°–127.5° C., is prepared by cleavage of the methoxy group of the compound of Example 4.

EXAMPLE 10

A solution of 5 g. of 4-(4-nitrobenzoyl)-2,6-di(t-butyl)phenol in 150 ml. of ethanol is treated with 40 ml. of ammonium sulfide solution. The mixture is heated at reflux for 2 hours then stirred without heating for about 16 hours. An additional 40 ml. of ammonium sulfide solution is added, and the mixture is heated at reflux for 4 hours more. After an additional 16 hours without heating, the mixture is extracted with dichloromethane, and the extracts are dried. Evaporation of the dried extracts provides a solid residue which is recrystallized twice from a benzene-hexane mixture to provide 4-(4-aminobenzoyl)-2,6-di(t-butyl)phenol as a light yellow solid, m.p. 164.5°–166.5° C.

| Analysis: | %C | %H | %N |
|---|---|---|---|
| Calculated for $C_{21}H_{27}NO_2$: | 77.5, | 8.36, | 4.3 |
| Found: | 77.9, | 8.3, | 4.1. |

What is claimed is:
1. A method for combatting inflammatory processes in a mammal which comprises administering to said mammal a dose less than the toxic amount but sufficient to inhibit inflammatory processes in said mammal of a compound of the formula:

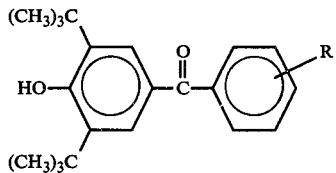

wherein R is amino.

* * * * *